United States Patent [19]
Yarmchuk

[11] Patent Number: 5,648,720
[45] Date of Patent: Jul. 15, 1997

[54] APPARATUS AND METHOD FOR PRODUCING A MAGNETIC IMAGE OF A CONDUCTIVE PATTERN USING EDDY CURRENTS

[75] Inventor: Edward John Yarmchuk, Somers, N.Y.

[73] Assignee: International Business Machines Corporation, Armonk, N.Y.

[21] Appl. No.: 36,773

[22] Filed: Mar. 25, 1993

[51] Int. Cl.$^6$ .......................... G01R 33/12; G01N 27/82
[52] U.S. Cl. .......................... 324/213; 324/262
[58] Field of Search .................. 324/213, 214, 324/215, 216, 228, 262, 529, 95, 235, 200

[56] References Cited

U.S. PATENT DOCUMENTS

| | | | |
|---|---|---|---|
| 3,344,345 | 9/1967 | Molina | 324/215 |
| 3,449,663 | 6/1969 | Schroeder et al. | 324/38 |
| 3,534,258 | 10/1970 | Förster | 324/37 |
| 3,596,143 | 7/1971 | Gruetzmacher et al. | 317/123 |
| 3,614,604 | 10/1971 | Reinshagen | 324/38 |
| 4,035,721 | 7/1977 | Lorenzi et al. | 324/213 |
| 4,072,895 | 2/1978 | Rogachev et al. | 324/238 |
| 4,447,778 | 5/1984 | Stumm | 324/213 |
| 4,755,753 | 7/1988 | Chern | 324/237 |
| 4,930,026 | 5/1990 | Kljuev et al. | 360/67 |
| 4,982,158 | 1/1991 | Nakata et al. | 324/263 |
| 5,008,620 | 4/1991 | Nonaka et al. | 324/213 |
| 5,028,866 | 7/1991 | Wiese | 324/95 |
| 5,053,704 | 10/1991 | Fitzpatrick | 324/235 |
| 5,109,196 | 4/1992 | Wikswo, Jr. et al. | 324/263 |
| 5,394,083 | 2/1995 | Jiles | 324/240 |

FOREIGN PATENT DOCUMENTS

| | | | |
|---|---|---|---|
| 1240194 | 7/1977 | United Kingdom | 324/200 |

Primary Examiner—Walter E. Snow
Attorney, Agent, or Firm—Heslin & Rothenberg, P.C.

[57] ABSTRACT

An apparatus and method for providing a fine line resistance image of a conductive pattern. A magnetic recording medium is placed in close proximity to the conductive pattern and a varying magnetic field is applied to the conductive pattern such that eddy currents in the conductive pattern are created. The eddy currents produce a magnetization pattern indicative of line resistance. The applied magnetic field is time varying and the varying magnetic field may be applied perpendicular to the recording medium or it may be applied in the plane of the recording medium.

21 Claims, 7 Drawing Sheets

APPARATUS AND METHOD FOR PRODUCING A MAGNETIC IMAGE OF A CONDUCTIVE PATTERN USING EDDY CURRENTS

TECHNICAL FIELD

This invention relates in general to imaging of conductive patterns and, in particular, to fine line resistance imaging of conductive patterns such that defects in the conductive patterns can be located.

BACKGROUND ART

The reliability of systems, such as computer systems, is impacted when defects exist in components of the system. In particular, if circuit lines located within a computer system have defects such as constrictions, thinned regions or cracks, the system may operate unpredictably. Therefore, techniques for detecting defects in circuit lines and other conductive patterns are continuously being sought. Such techniques include, for example, using a computer to analyze optical images in order to detect and locate visually obvious defects on exposed circuit lines; taking direct measurements of line resistance in order to detect defects that are large enough to significantly affect the total line resistance; and detecting non-linear resistance effects due to localized heating at a partial electrical blockage to detect defects in exposed or buried conductors.

Described below are a couple of examples of techniques for detecting defects. For example, in U.S. Pat. No. 4,072,895, entitled "Eddy Current Converter for Non-Destructive Testing of Electrically Conducting Coating in Holes of Printed Circuit Boards," issued on Feb. 7, 1978, to Rogachev et al. a technique for detecting defects is described. The eddy current converter described in U.S. Pat. No. 4,072,895 is used for non-destructive testing of electrically conductive coating in holes of printed circuit boards and not of circuit lines themselves. The eddy current converter comprises a cylindrical frame enveloped by an exciting winding and a measuring winding. The coils of the exciting and measuring windings extend along the generatrices of the cylindrical frame. The converter is inserted into a hole of a printed circuit board being tested.

In another example, a method and apparatus for detecting flaws in ferromagnetic materials, such as alloys containing iron, cobalt or nickel, are described in U.S. Pat. No. 5,008,620 entitled, "Leakage Flux Flaw Detection Method and Apparatus Utilizing a Layered Detector," issued on Apr. 16, 1991, and assigned to Agency of Industrial Science and Technology; Ministry of International Trade and Industry.

The leakage flux flaw detection technique described in U.S. Pat. No. 5,008,620 comprises applying one surface of a magnetic recording material to the test surface of a test material, overlaying the other surface of the magnetic recording material with a layer of magnetic material with the intervention of a non-magnetic layer and forming a magnetic path that passes through the test material. The magnetic path facilitates the flow of the leakage flux, increases the magnetization of the magnetic recording material and enables flaws to be detected.

The previously known techniques for detecting defects typically involve the detection of small defects within large metal areas and not the detection of conductive pattern defects in fine line geometry. Many of the techniques require electrical contact to the device being tested and only provide point probing information rather than image information.

Therefore, a need exists for a method and apparatus for providing a fine line resistance image of a conductive pattern. Further, a need exists for a mechanism for detecting defects, which does not require electrical contact, and applies to non-magnetic conductors of fine line geometry. Further, a need exists for a mechanism which provides image information rather than point probing information. Yet another need exists for a mechanism which provides for the imaging of lines using a low inductance head structure that is capable of producing high field strengths at a high frequency.

DISCLOSURE OF THE INVENTION

The shortcomings of the prior art are overcome and additional advantages are provided through the provision of an apparatus for providing a fine line resistance image of a conductive pattern. The apparatus includes means for applying a varying magnetic field, such as a time varying magnetic field, to the conductive pattern and magnetic recording means disposed in close proximity to the conductive pattern for storing a magnetization pattern indicative of line resistance produced by eddy currents in the conductive pattern.

In one embodiment, the applying means includes a predetermined amount of low conductivity magnetic material having a slot, a coil passing through the slot and means for applying current to the coil.

In another aspect of the invention, a method for providing a fine line resistance image of a conductive pattern is provided. A varying magnetic field is applied to the conductive pattern wherein a magnetization pattern indicative of line resistance is produced by eddy currents in the conductive pattern. The magnetization pattern is stored on a magnetic recording medium.

In one embodiment of the invention, the varying magnetic field is time varying and the magnetic field is applied perpendicular to the magnetic recording medium. In another embodiment, the magnetic field is applied in a plane of the magnetic recording medium.

The apparatus and technique of the present invention provide for a fine line resistance image of a conductive pattern. The image is capable of being formed by a low inductance head structure that can produce high field strengths at a high frequency. In addition, large areas are advantageously capable of being imaged with the technique of the present invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention will be apparent from the following detailed description taken in conjunction with the accompanying drawings in which:

FIG. 9b shows an optical microscope image of the same region depicted in FIG. 9a.

BEST MODE FOR CARRYING OUT THE INVENTION

Figure 1:
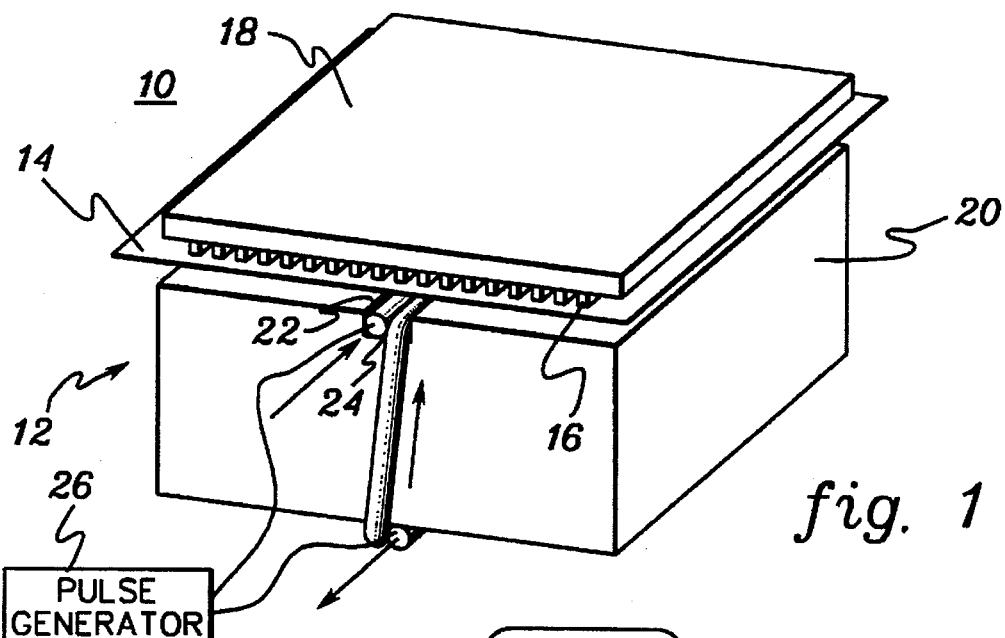
FIG. 1 depicts one embodiment of an imaging apparatus, in accordance with the principles of the present invention.

One embodiment of an apparatus for providing a fine line resistance image of a conductive pattern is depicted in FIG. 1. Referring to FIG. 1, an imaging apparatus 10 includes, for instance, a recording head 12 (commonly referred to as a ring-gap head), a recording medium 14 and a conductive pattern 16, which is located on an insulating substrate 18. Each of these components is described in detail below.

As one example, recording head 12 is manufactured of a non-conductive ferrite block 20 and is approximately 18 millimeters wide. Cut into ferrite block 20 is, for instance, a 0.25 millimeter wide by 0.15 millimeter deep slot 22. Running through slot 22 are two turns of #38 copper wire 24. The arrows depicted in FIG. 1 illustrate the direction of current through the copper wire. It will be apparent to those skilled in the relevant art that the recording head can be smaller or larger than 18 mm wide and that 18 mm is only one example. However, wider heads have a higher inductance and require higher pulse voltage. Further, other materials for the recording head are suitable as long as the conductivity of the material is sufficiently low such that the eddy currents within the material are weak enough to allow the magnetic flux to pass at the desired frequency. It will also be apparent that the slot size and number of turns of wire can vary. For instance, a slot which is 0.025 mm wide, 0.38 mm deep and filled with a single turn conductor is also sufficient.

Recording medium 14, which consists of, for instance, a sheet of magnetic recording tape, is separated from recording head 12 by approximately 0.05 millimeters (i.e., equal to the thickness of the recording medium plus the backing material of the tape (approximately 0.025 mm each)). The separation is maintained by holding the head in light contact with the back of the recording tape by using, for example, a vacuum chuck, pressurized air to form an air bearing between the recording head and the tape, or precise mechanical fixtures to position the conductive pattern and recording tape relative to the head.

Insulating substrate 18 includes, for instance, a ceramic chip-carrier containing a plurality of parallel circuit lines (i.e., conductive pattern 16), each of which is 0.025 millimeters in width.

In accordance with the principles of the present invention, imaging apparatus 10 is used in providing a fine line resistance image of, for example, one or more of the circuit lines on the insulating substrate. The image is used in one embodiment to detect defects, such as constrictions, thinned regions, cracks or holes in the circuit lines.

Figure 2:
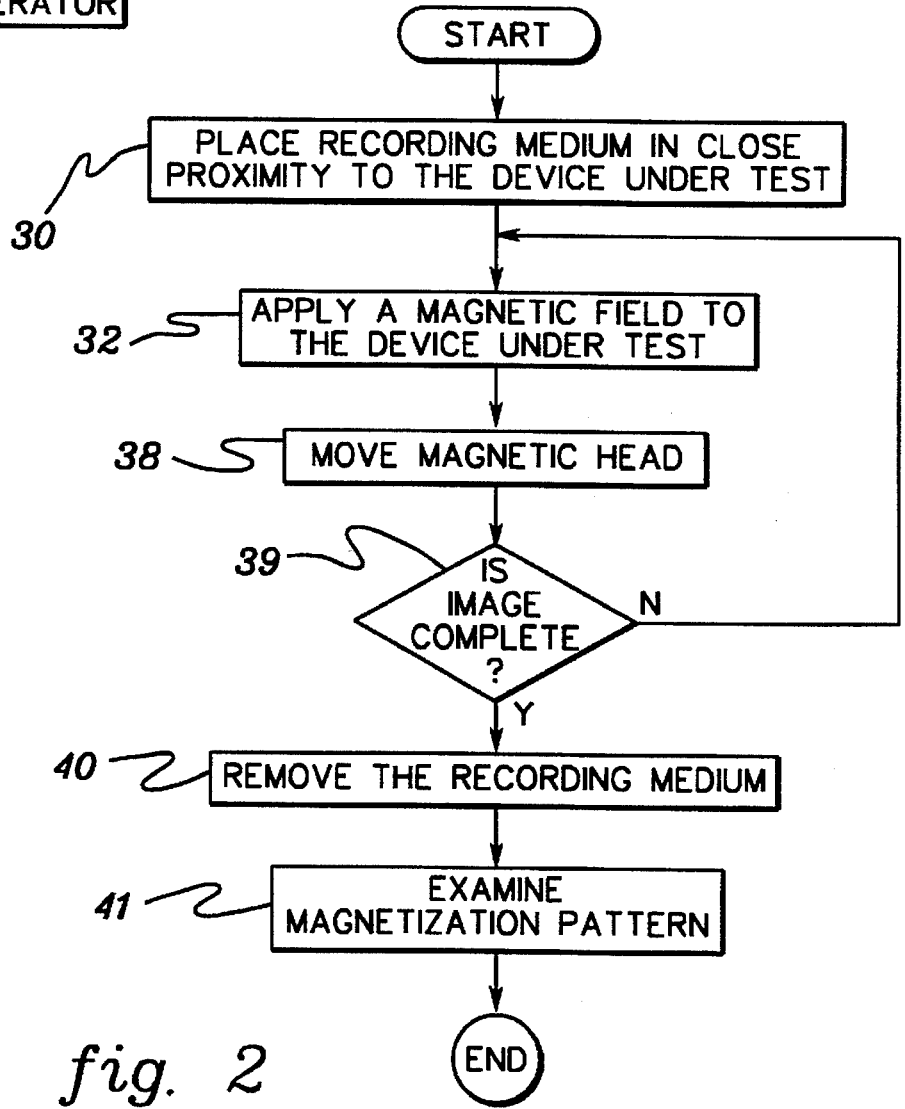
FIG. 2 depicts one example of the logic associated with one embodiment of an imaging technique, in accordance with the principles of the present invention.

Referring to FIG. 2, one embodiment of the technique of the present invention for providing an image is described in detail. Initially, recording medium 14 is placed in close proximity to the device under test, STEP 30 "PLACE RECORDING MEDIUM IN CLOSE PROXIMITY TO THE DEVICE UNDER TEST." In particular, a 0.05 mm thick sheet of recording tape is held in close proximity by mechanical pressure or a vacuum chuck (to name a couple of examples) to the circuit lines to be tested. It is preferred that the gap between the recording tape and the circuit lines be less than about half of the width of the circuit lines.

Subsequent to placing the recording medium in close proximity to the circuit lines, a magnetic field is applied to conduction pattern 16, STEP 32 "APPLY A MAGNETIC FIELD TO THE DEVICE UNDER TEST." In particular, in one embodiment, the magnetic field is applied to the substrate, circuit lines and recording medium. In applying the magnetic field, recording head 12 is used, which is driven by approximately 12 to 16 amperes of current passed through copper wire 24. The current is supplied by a known pulse generator 26. The current waveform has, for instance, a pulse length of 1 microsecond and a turn-off time (90%–10%) of about 10 nanoseconds. In applying the magnetic field to the conductive pattern, various field configurations and time dependencies may be used. For instance, the magnetic field can be applied perpendicular to the recording medium or in the plane of the recording medium, and the time dependence can be either very short pulsed with a fast rise and fall or a longer pulse with a fast falling edge.

Figure 3A:
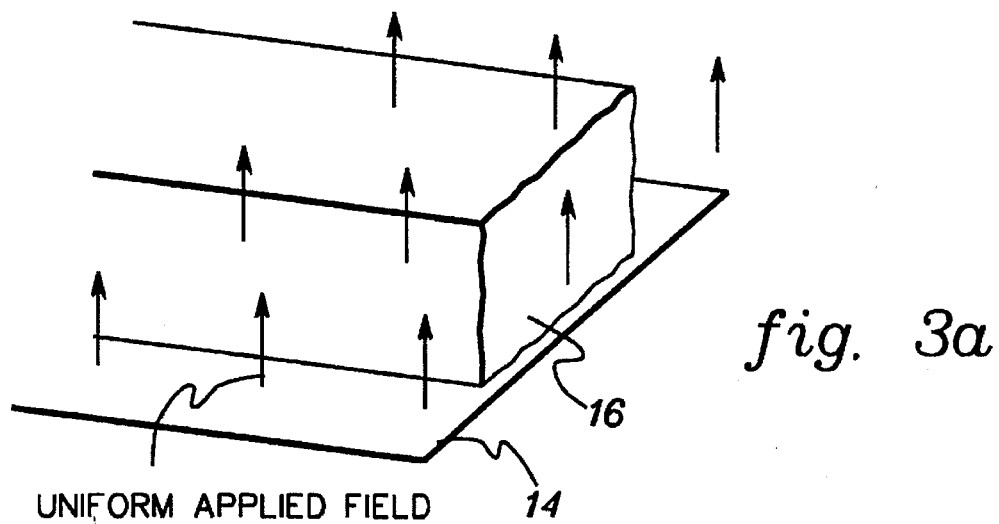
FIG. 3a depicts one example of a uniform applied field perpendicular to the plane of the recording medium, in accordance with the principles of the present invention.
Figure 3B:
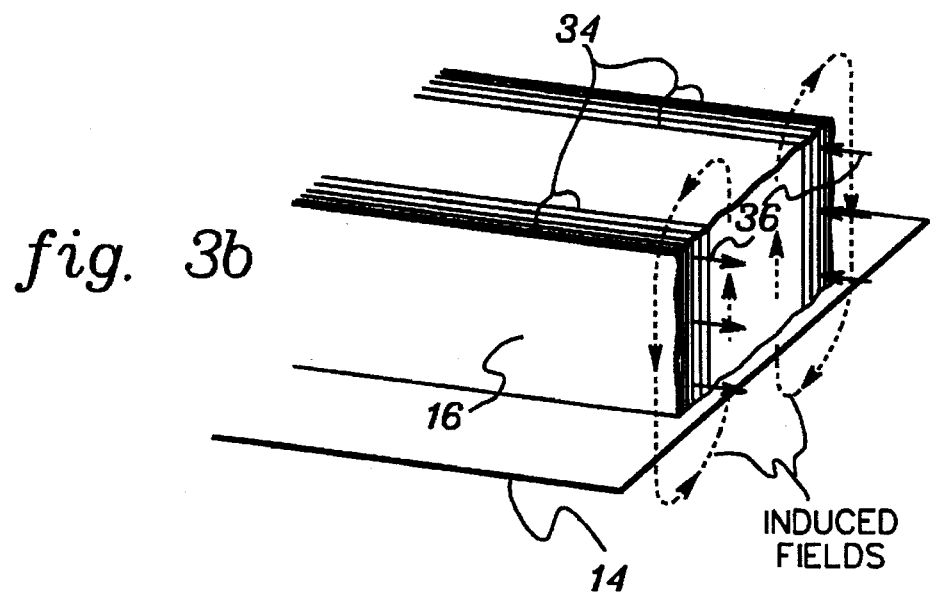
FIG. 3b depicts one example of a cross-section of a circuit line with a trapped flux recording and a perpendicular field, in accordance with the principles of the present invention.

As stated above, in one example, the magnetic field configuration is a perpendicular applied field and the time dependence is a long pulse of approximately 60 nanoseconds with a turn-off time of 4 nanoseconds (i.e., for the circuit lines described above). With this configuration, just before the applied magnetic field is turned off, the magnetic field is uniform (FIG. 3a) and has completely penetrated circuit line 16. As the applied magnetic field is turned off, eddy currents 34 (FIG. 3b) are induced in circuit line 16 such that the magnetic flux density within the line is maintained. For a long, uniform circuit line, as in FIGS. 3a–3b, the eddy currents flow in sheets along the two sides of the line, as indicated by reference numeral 34. (In these figures, the exposed end of the line is meant to indicate a cross-section through an otherwise continuous circuit line. Further, the arrows referenced by numeral 36 coming out of and into eddy currents 34 indicate the direction of the eddy currents.) The induced fields are shown in the vicinity of the cross-section, but are actually present everywhere along the line. The direction of the induced fields are indicated by the dashed lines and arrows.

Outside the circuit line, the magnetic field from the eddy currents is opposite the original applied field direction. The distribution of current within the sheets can be precisely determined only through numerical computation, but can be understood approximately through application of the theory of the skin effect (see *Electromagnetic Fields and Waves*, by Paul Lorrain and Dale Corson, W. H. Freeman and Company, San Francisco, 1970, which is hereby incorporated by reference). In this effect, a sinusoidally varying magnetic field applied to a conductor generates eddy currents that are at maximum at the edge of the conductor and drop off exponentially with distance into the conductor. The decay length for the exponential is the skin depth. The square of the skin depth is proportional to the resistivity of the conductor divided by the frequency of the applied field. A field that is turned off with a fall time T consists of a superposition of many frequencies, but the dominant components are close to $1/(2 \times Pi \times T)$. For T=4 nanoseconds, this frequency is about 40 MHz. At this frequency, the skin depth for copper is about 0.01 mm.

If the applied field is sufficiently strong and is turned off sufficiently rapidly, in accordance with the principles of the present invention, the eddy currents generated in the circuit lines under test produce a magnetic field which exceeds the coercivity of the recording medium (typically several hundreds of Oersted) and, therefore, leaves behind a remnant magnetization pattern indicative of line resistance in the recording tape. The strength of the remnant magnetization varies with the magnitude of the eddy currents, which in turn depend in inverse fashion on the resistance per unit length of the circuit lines. Thus, regions of circuit lines with higher resistance per unit length produce lower remnant magnetization. The precise relationship between the line resistance per unit length, the magnitude of the eddy currents and the remnant magnetization can only be determined through detailed numerical computation. The general features, as described above, have been established empirically.

Figure 3C:
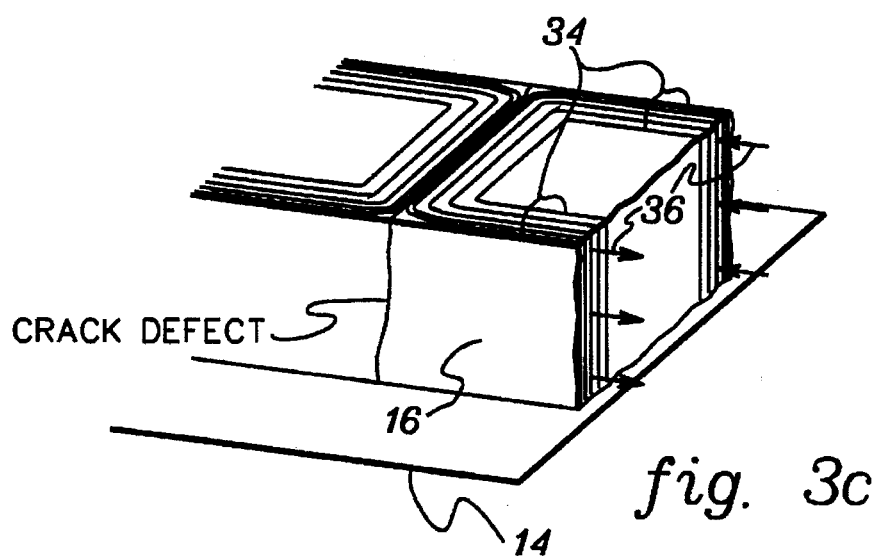
FIG. 3c illustrates one example of the effects of a local blockage of current due to a crack in a circuit line, in accordance with the principles of the present invention.

The resistance per unit length can vary as a result of differences in the thickness or width of the circuit lines, as might occur intentionally in different portions of a circuit pattern, or could arise from local defects, such as cracks, thinning, notching or even a resistivity change due to impurities. Referring to FIG. 3c, the effects of a local blockage of currents, for example, due to a microscopic crack, are illustrated. (In all of the figures, like numbers reference similar components.) The sheets of eddy currents 34 flowing along either side of conductor 16 are bent around to join each other in the vicinity of the blockage. The sheets of current maintain their characteristic thickness equal to the skin depth as they bend around, thereby producing a region of reduced net current (the currents on the two sides of the blockage are opposite and close together) that is about as long as the skin depth. This is an important feature for the detection of microscopic crack-like defects, since the spatial resolution needed to identify a defect in the magnetic image need only be equal to a skin depth, not the size of the physical defect (which is what an optical defect detector would require).

If severe enough, a defect can lead to complete elimination of the remnant magnetization (a "hole" in the image of a circuit line). Weaker defects produce a local reduction in the strength of the remnant magnetization pattern. Thus, the amount of modulation of the magnetization can serve as an indicator of defect severity. Roughly speaking, the relative severity of a defect is determined by the amount of excess resistance associated with the defect as compared to the normal line resistance over a length equal to a skin depth. For example, if a defect contributes an excess resistance equal to the resistance of a good line segment one skin depth long, it is roughly comparable in effect to a halving of the line width. The amount of modulation corresponding to this can be determined by measuring the magnetization produced by circuit lines that are half as wide as the line under test. For lines that are close to the limit of resolution (width=2×skin depth), the modulation is likely to be nearly 100% since lines half as wide fall below the coercivity threshold for imaging. Lines that are wider have moderate modulation, while extremely wide lines (which tend to saturate the recording medium) produce little or no modulation. Thus, for a given choice of skin depth, there is a range of line widths which are optimum for providing sensitivity and the ability to discern defect severity. This range can be adjusted by varying the turn off time for the applied field, which is controlled by the fall time of the current pulse used to generate the field.

In one particular example, the applied field strength and turn off time are sufficient to produce imaging in some portion of the region where the field is perpendicularly oriented. In this region, the imaging takes place in the manner described above and illustrated by FIGS. 3a-3c. Specifically, a magnetic head structure with a single turn conductor and a head gap of 0.125 mm, pulsed with a peak current of 60 A, a duration of 60 nanoseconds and a fall time of 4 nanoseconds, having a separation of 0.05 mm from the circuit lines, meets the applied field strength and turn off time conditions for circuit lines 0.007 mm thick by 0.026 mm wide, in contact with an iron oxide-type recording medium having a coercivity of about 300 OerSted.

Figure 4:
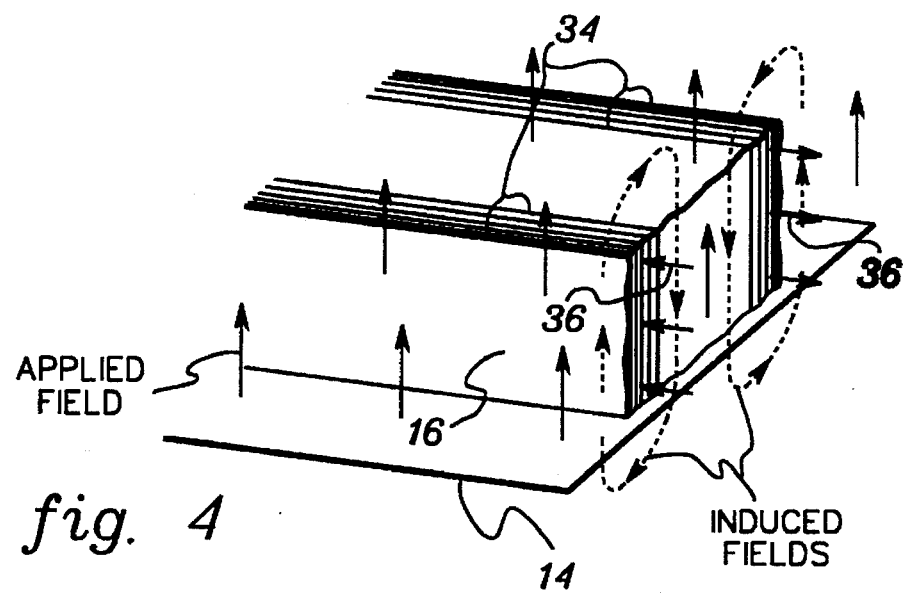
FIG. 4 depicts one example of a cross-section of a circuit line with an expelled flux recording and a perpendicular field, in accordance with the principles of the present invention.

In another embodiment, the magnetic field is also applied in a field perpendicular to the recording medium, such as recording tape 14 of FIG. 1. However, only a very brief pulse of current is applied to copper 24. In particular, the total pulse duration of the current is approximately equal to the fall time. Referring to FIG. 4, with this configuration, at the moment of peak current for a very brief pulse, the magnetic field does not have time to penetrate the conductor and eddy currents 34 produce a magnetic field inside the conductor that just cancels the applied field.

Figure 5:
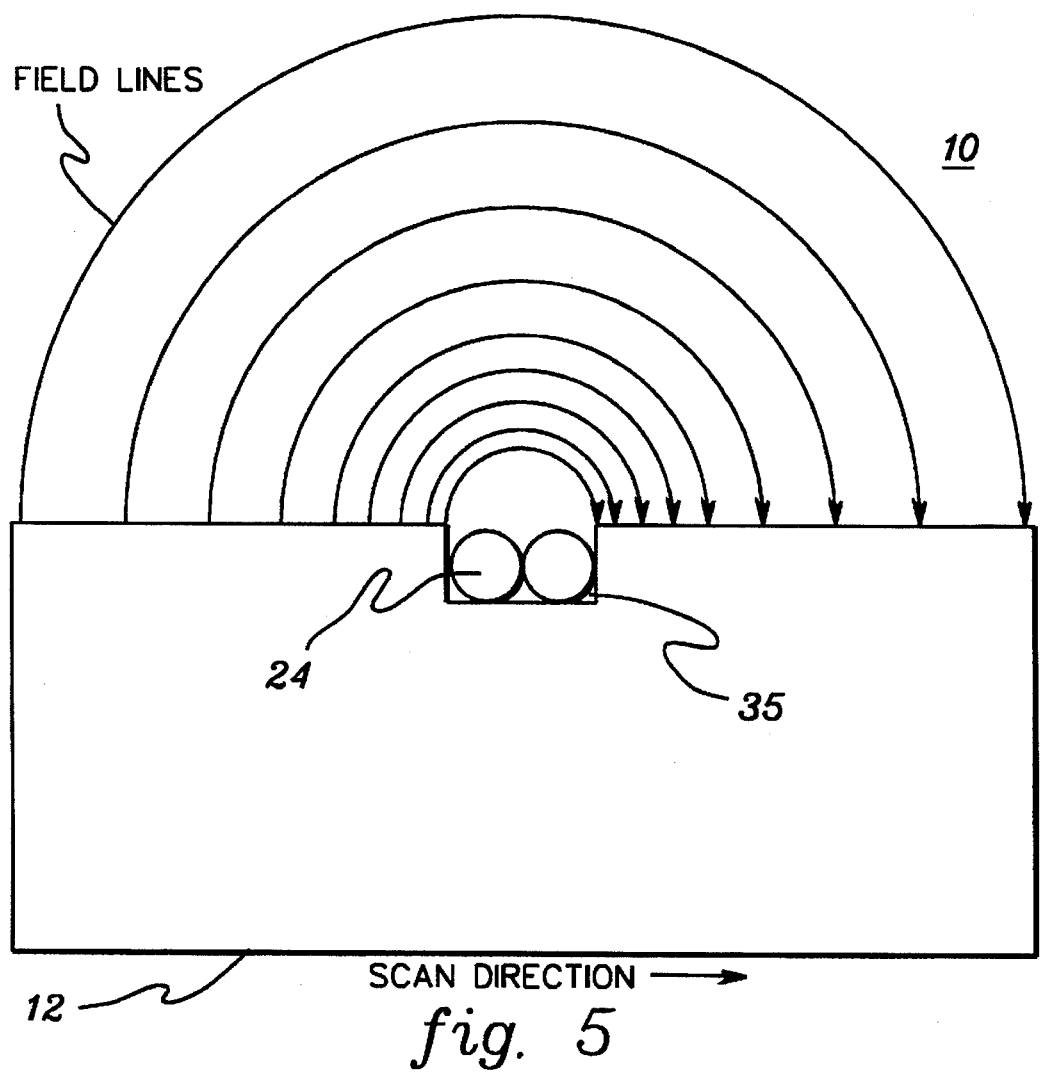
FIG. 5 illustrates one embodiment of a side view of the recording head structure of FIG. 1, as well as the magnetic field lines existing outside of the magnetic material, in accordance with the principles of the present invention.

In yet another embodiment, the magnetic field may also be applied in the plane of the recording medium. Referring to FIG. 5, a side view of recording head 12 of imaging apparatus 10 is shown together with the magnetic field lines as they exist in the space outside of the magnetic material. It can be seen that both orientations (i.e., perpendicular and in-plane) of the applied field are present. Directly above the head gap (designated by reference numeral 35), the field is in-plane with respect to the circuit lines and recording medium, while off to either side, the field becomes perpendicular. The strength of the magnetic field is constant along each of the approximately circular field lines, but decreases with distance from the head gap, as indicated by the spacing between field lines in the figure.

Figure 6A:
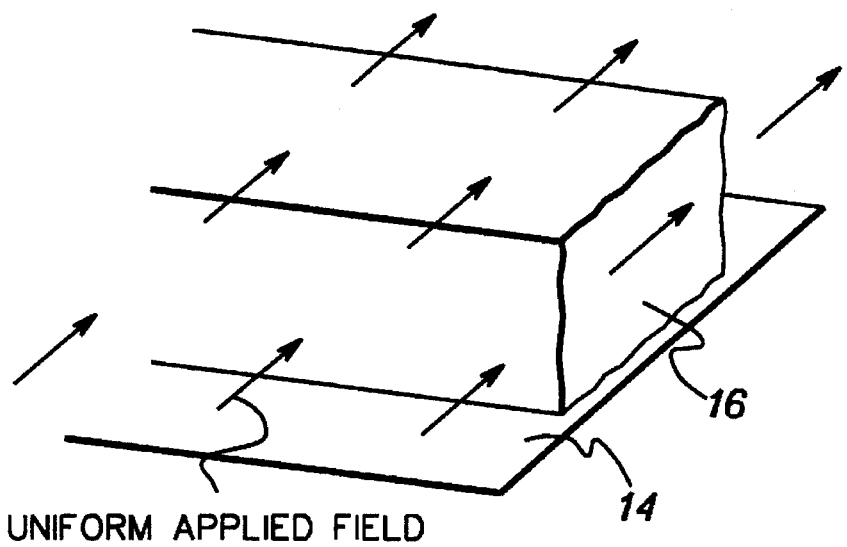
FIG. 6a depicts one example of a uniform applied field in the plane of the recording medium, in accordance with the principles of the present invention.
Figure 6B:
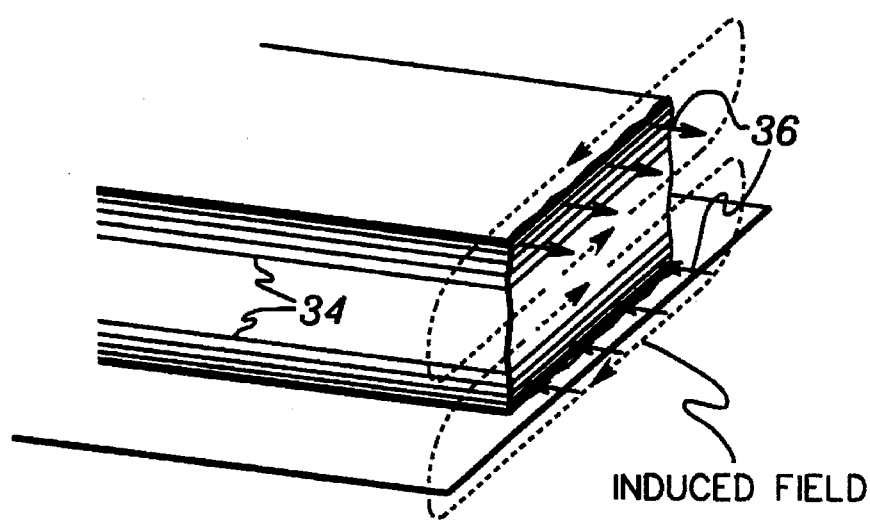
FIG. 6b depicts one example of a cross section of a conductor line with an in-plane field and a trapped flux recording, in accordance with the principles of the present invention.

Referring to FIGS. 6a and 6b, one embodiment of the in-plane mode configuration with a relatively long pulse is described. Before the current is turned off, the magnetic field is applied uniformly in the plane of recording medium 14 (FIG. 6a) and completely penetrates circuit line 16. (In one embodiment of the in-plane mode, conductor line 16 is 0.05 mm thick and located on an epoxy-glass board.) Subsequent to turning off the current, eddy currents 34 (FIG. 6b) are induced in the conductor line in such a way as to maintain the magnetic flux density within the line. Outside line 16, a magnetic field is created that is opposite to the applied field, as shown by the arrows within dashed lines. The recording medium is pre-saturated in the direction of the applied field. To be effective, an induced field exceeds the coercivity of the recording medium so as to produce reversal or at least reduction of the magnetization. The remnant magnetization is directed across the conductor line and is easily detected with a recording head or powder due to its strong divergence.

Figure 7:
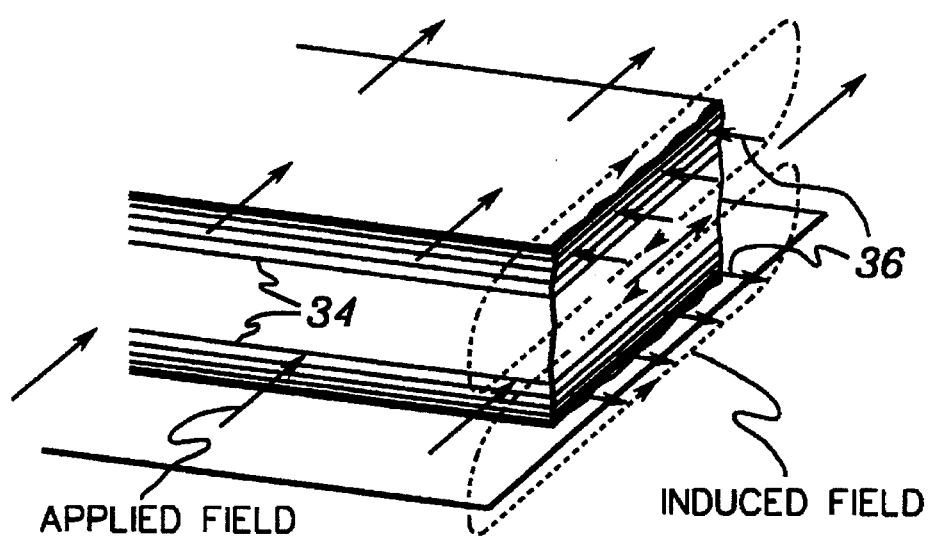
FIG. 7 depicts one embodiment of a cross-section of a conductor line with an in-plane field and an expelled flux, in accordance with the principles of the present invention.

In yet another embodiment of the present invention, the magnetic field is applied to conductor lines to be tested, such as 0.05 mm thick circuit lines on an epoxy-glass board, in the plane of the recording medium and a very brief pulse (for this thickness of lines) having a duration of about 100 nanoseconds is applied. Referring to FIG. 7, in this configuration, the applied field does not have time to penetrate conductor 16. Eddy currents 34 produce an induced field inside the conductor that just cancels the uniform applied field. Outside the conductor, the induced field is in the same direction as the applied field. If the recording medium is pre-magnetized opposite to the applied field and the field strength is adjusted to be slightly less than the coercivity of the recording medium, then selective reversal of the medium occurs only where the added field from the conductor is present.

Referring once again to FIG. 2, subsequent to applying a magnetic field to the circuit pattern to be tested, magnetic head 14 is moved by a small amount in the direction perpendicular to slot 22, as shown by the arrow indicating scan direction in FIG. 5, STEP 38 "MOVE MAGNETIC HEAD" (FIG. 2). In one embodiment, the amount of movement between steps is small enough that the region in which perpendicular imaging occurs overlaps that produced in the preceding step. For the specific head structure, recording medium and circuit lines described above, the movement is less than approximately 0.1 mm in order for the overlapped images to properly merge. Larger steps result in a periodic modulation of the final image at a period equal to the step size.

Subsequently, the total displacement of the head from its starting position is checked to see if it exceeds a predetermined amount corresponding to the length of the region to be imaged, INQUIRY 39 "IS IMAGE COMPLETE?" If the displacement does not exceed this amount, the process returns to STEP 32 "APPLY A MAGNETIC FIELD TO THE DEVICE UNDER TEST." In applying the magnetic field after the head is moved, the current pulse has, in one example, a turn-on time which is substantially longer than the turn-off time. This can be accomplished, in one example, by placing a diode in parallel to the head coil (not shown) in pulse generator 26. Subsequent to applying the magnetic field, the process continues as described with reference to FIG. 2.

If the result of INQUIRY 39 is that the total displacement does exceed the desired amount, then the recording medium is removed, STEP 40 "REMOVE RECORDING MEDIUM." After the recording medium is removed, the remnant magnetization pattern is examined, STEP 41 "EXAMINE MAGNETIZATION PATTERN."

In accordance with the principles of the present invention, an image of the magnetization pattern can be made visible by using fine magnetic powders and a television system to image the pattern or by using Kerr effect imaging. It will be apparent to one of ordinary skill in the art that other imaging techniques may also be used and that magnetic powders and Kerr effect imaging are only two examples. After visualizing the magnetization pattern, the image may be analyzed to determine if any holes in the magnetization pattern exist. A hole in the magnetization pattern is evidence that an electrical defect in the circuit pattern exists. The size of the hole in the magnetization pattern is determined by the skin depth of the conductor and the severity of the electrical blockage rather than by the physical size of the defective region.

In addition to the above, it is also possible to measure the pattern of magnetization by a scanned magnetic readback head such as one found in, for instance, a videocassette recorder or a disk storage device. In one example, an inductive readback head is used to scan across the magnetization image from a ceramic chip carrier with circuit lines of thickness 0.007 mm and varying widths down to a minimum of 0.025 mm, produced using the head structure and current pulse conditions described above. The inductive head is similar to vertical magnetic recording heads used in some digital magnetic storage applications. This type of head is well suited for detecting perpendicular components of magnetization.

Figure 8A:
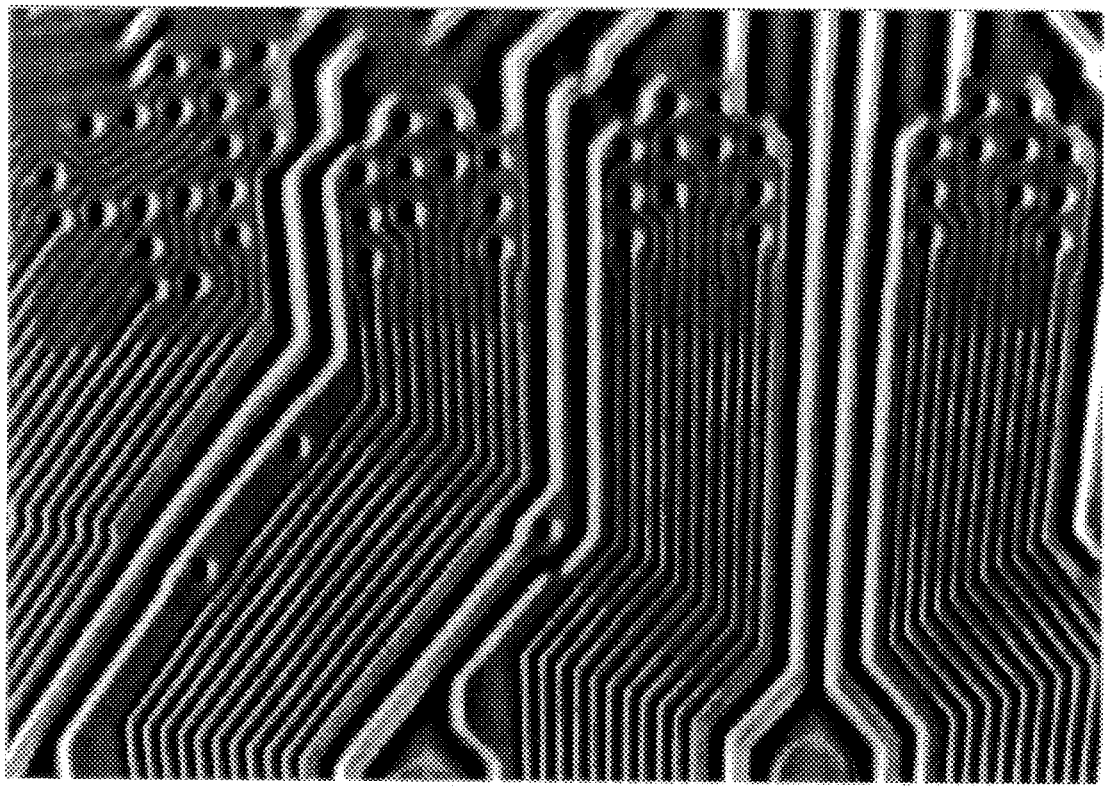
FIG. 8a depicts an image of a conductive pattern produced in accordance with the principles of the present invention.
Figure 8B:
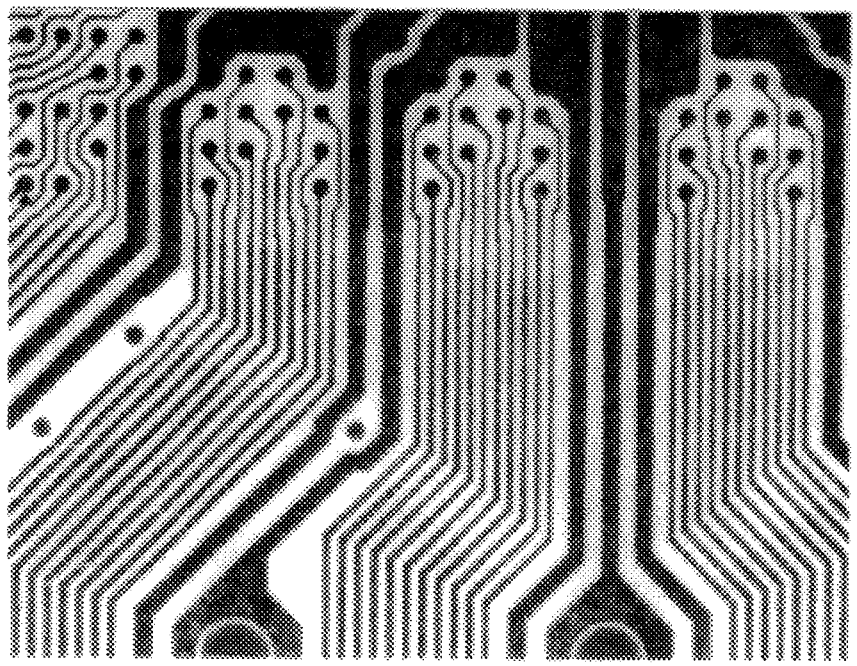
FIG. 8b depicts the results of the corresponding region of FIG. 8a, produced using a microscope and an attached camera.

FIG. 8a shows an image produced from digitized readback signals obtained by scanning the inductive head across a recording tape containing a magnetization image of the ceramic chip carrier circuit lines. The scanning is accomplished in a manner similar to that in a disk file by spinning a disk-shaped piece of tape past the readback head which is moved gradually in the radial direction. The image of FIG. 8a is produced by assigning a gray value to each pixel in direct proportion to the instantaneous readback voltage at that location. The readback voltages are bipolar; positive voltages correspond to darker pixels, negative voltages to lighter pixels. FIG. 8b shows a photograph of the corresponding region of the ceramic chip carrier made in the usual fashion, using a microscope with an attached camera. The slight distortion of the magnetization image arises from the fact that the circumferential arcs corresponding to the readback waveform were plotted as straight horizontal lines. This can be corrected during the plotting of the image or can be eliminated entirely through the use of other scanning means, such as X-Y translation stage, which would allow the capture of data in rectilinear coordinates.

FIG. 8a illustrates many of the features of this technique. It can be seen that the fine lines are discernible at almost all angles, as expected for the perpendicular mode of recording. The variation of the signal strength with the line width is also evident. Careful examination shows numerous locations with "holes" in the magnetization image, especially in the fine line regions. These correspond to defects that were introduced artificially using a laser to nearly sever the circuit lines.

Figure 9A:
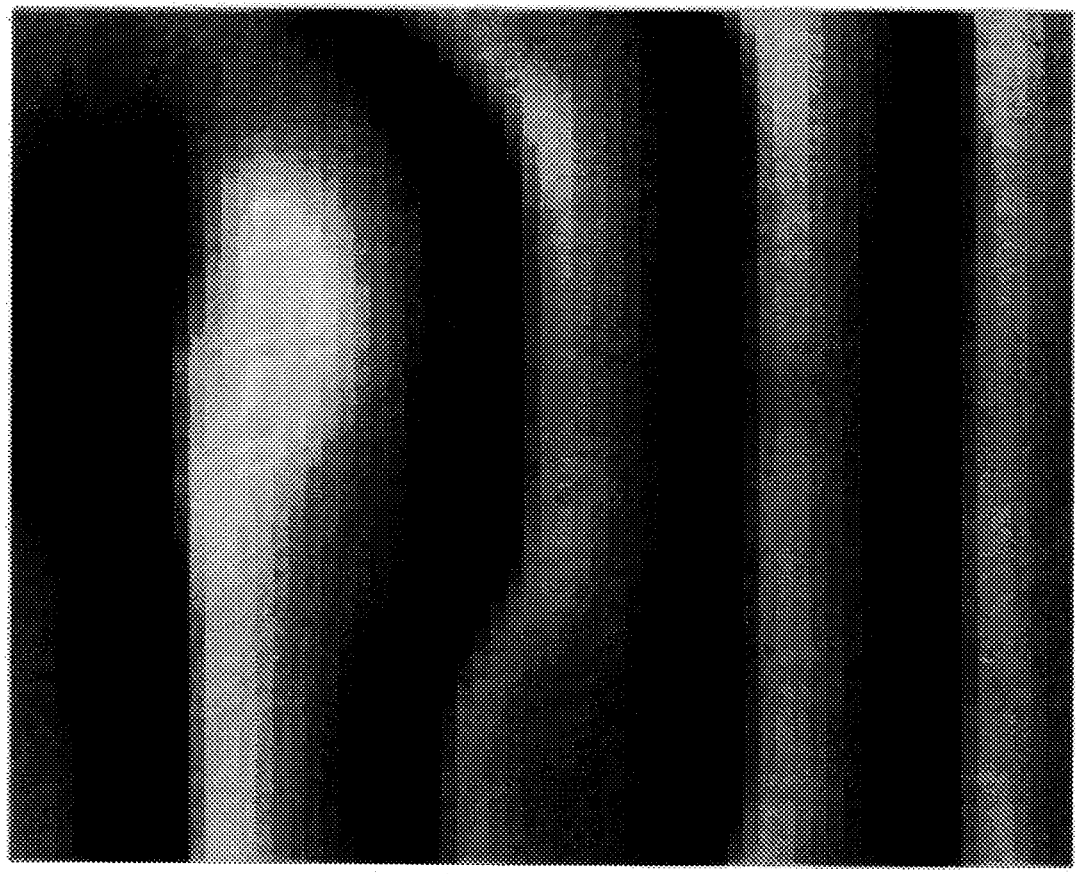
FIG. 9a depicts one example of a defect image, in accordance with the principles of the present invention.
Figure 9B:
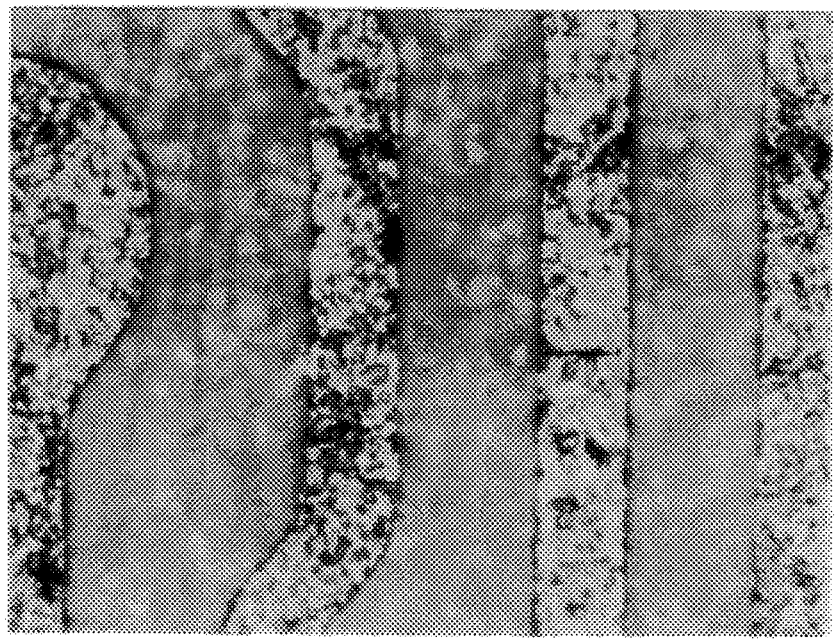

A clearer illustration of a defect image is shown in FIG. 9a. This is a more highly magnified view of a region of the ceramic chip carrier containing the finest lines. FIG. 9b shows the optical microscope image of the same region. In this case, the defect was created using a focused ion beam to produce a 0.001 mm wide cut through the line and 90% of the way across it. Note that the defect appears clearly in the magnetization image despite the extremely narrow extent of the physical defect.

Referring again to FIG. 8a, there is some anisotropy present due to the use of an inductive head in the readback process. This is most apparent where lines abruptly change direction but not width. (Because the inductive read head output signal is proportional to the time rate of change of the magnetization under the head, the peak to peak signal varies as the sine of the angle between the scan direction and the line.) It is possible to perform signal processing operations to compensate for this effect. One example is to integrate the signal along the scan direction, thereby offsetting the differentiation effect of the inductive element. Alternatively, the problem can be eliminated by using a magnetoresistive sensor for the readback. Such a sensor directly measures magnetic flux, rather than its time derivative. Other possible schemes involve reading the magnetization image twice with orthogonal scan directions.

It will be apparent to those skilled in the relevant art that various recording media can be used (isotropic, perpendicular, longitudinal) having various coercivities, squarenesses, etc., which can be employed in the technique of the present invention. In addition, a great deal of variation is possible, depending on the circuit line dimensions, the pulse generator peak current and fall times, currents, gaps, voltage, the head gap, head width, number of turns, and the type of recording medium. The general trend is that circuit lines that are finer or have higher resistivity require shorter fall times for good imaging. That is, the resistance per unit length determines the strength of the image for a given fall time. The higher the resistance is, the lower the image strength. The range of sensitivity for a given fall time is limited so one would adjust the fall time to provide optimum response for particular line geometries of interest. In defect detection applications, one would probably be interested in the finest lines present, since these would be most susceptible to being defective. To be more specific about fall times, it is observed that a 5 nanoseconds fall time is good for copper lines 0.007 mm thick and 0.025 mm wide, while 0.04 mm thick by 0.075 mm wide copper lines can be imaged with a 200 nanoseconds fall time.

The technique and apparatus of the present invention advantageously provide the capability of imaging large areas of a circuit board. In particular, a low inductance recording head capable of producing high field strengths at a high frequency is used. The remnant magnetization images from pulse recordings at successive locations along the device under test merge perfectly into a 2-D image of the conducting lines.

Figure 10:
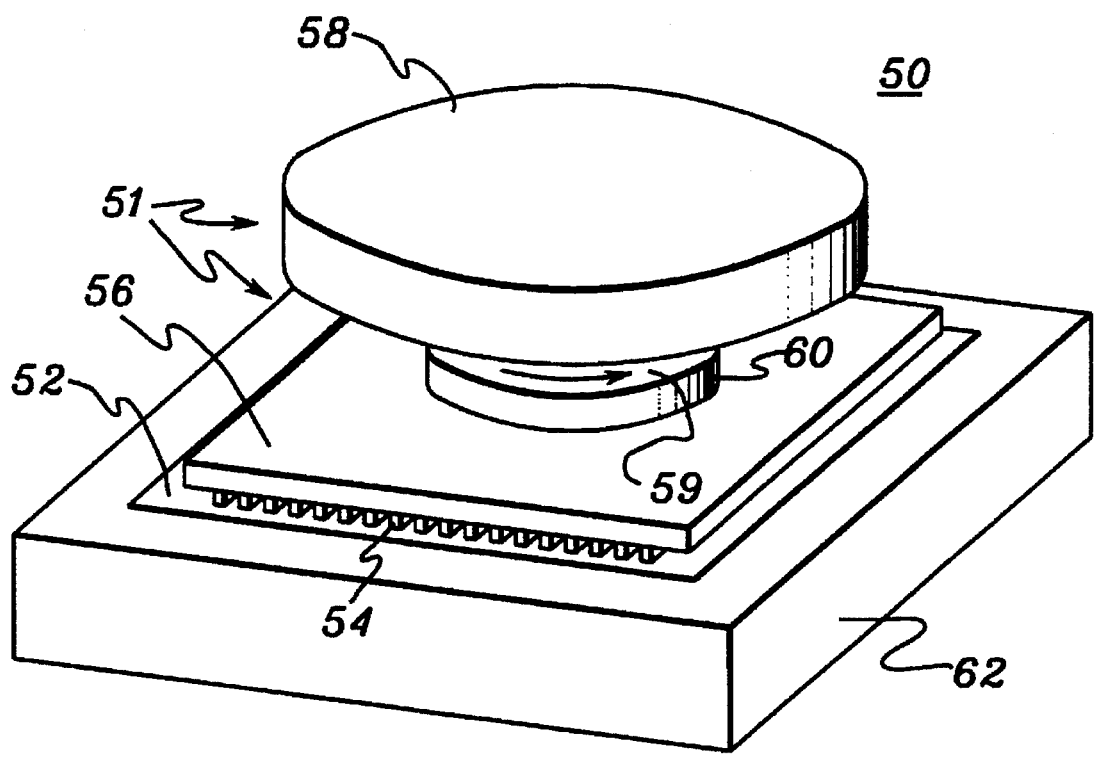
FIG. 10 depicts another example of an imaging apparatus, in accordance with the principles of the present invention.

Referring to FIG. 10, another example of an imaging apparatus 50, is described. Imaging apparatus 50 includes, for example, a recording head 51, a recording medium 52 and a conductive pattern 54 located on an insulating substrate 56. Each of these components is described in detail below.

Recording head 51 includes, for instance, a pedestal 58, a four-turn coil 59 wound around a post 60 connected to pedestal 58, and a planar ferrite block return path 62. A region of uniform, perpendicular field is provided between the bottom of post 60 and return path 62. Pedestal 58 is, for instance, 1 millimeter high, 25 millimeters in diameter and manufactured of ferrite. The post is also made of ferrite and is, for example, 0.6 mm high and 12 mm in diameter. (Recording head 51, including the pedestal, post and return path, can be manufactured of other materials. The material should be low conducting, such that the eddy currents within the material are weak enough to allow the magnetic flux to pass at the desired frequency.) A gap of approximately 0.4 mm is defined between post 60 and return path 62 and located within the gap are recording medium 52 and insulating substrate 56. A magnetic field generated by the coil exits the bottom of the post, crosses the gap, enters the return path block (where it spreads out), and re-emerges upward (outside of the post region) to return to the pedestal (through an air path equal to the gap, plus the post height). The field converges toward the post where it completes the loop. (Field lines form closed loops.)

Recording medium 52, is for instance, approximately 0.025 millimeters of magnetic recording tape and is held in close proximity to conductive pattern 54. In particular, recording medium 52 is placed directly against the flat return path where the field is almost perfectly perpendicular.

In one example, insulating substrate 56 is a ceramic chip-carrier with a plurality of conductive lines forming conductive pattern 54 on the top surface. The substrate is approximately 0.4 millimeters thick and each of the plurality of circuit lines can be of varying sizes. For instance, the lines can be 0.007 mm thick and 0.025 mm wide. It will be apparent to one of ordinary skill in the art that conductive pattern 54 may include a number of patterns and that circuit lines is only one example.

In accordance with the principles of the present invention, imaging apparatus 50 may be used with the technique described in detail with reference to FIG. 2 in order to provide an image of a device under test. That is, eddy currents caused by a varying magnetic field applied to the device under test produce a magnetic field which creates a magnetization pattern indicative of line resistance. The magnetization pattern is stored on a magnetic recording medium.

Described above are various mechanisms for providing images of conductive patterns. In particular, mechanisms for providing fine line resistance images of circuit lines and other conductive patterns are described. Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An apparatus for providing a fine line resistance image of a conductive pattern comprising:

means for applying a rapidly varying magnetic field to said conductive pattern such that eddy currents are induced in said conductive pattern and the eddy currents produce a secondary magnetic field in the vicinity of the conductive pattern, strength variations of the secondary magnetic field being indicative of line resistance of said conductive pattern and being dominant over any other local magnetic field variations; and a magnetic recording medium disposed in close proximity to said conductive pattern for directly capturing an image of said secondary magnetic field.

2. The apparatus of claim 1, further comprising visualizing means for examining said stored magnetization pattern.

3. An apparatus for providing a fine line resistance image of a conductive pattern comprising:

means for applying a rapidly varying magnetic field to said conductive pattern such that eddy currents are induced in said conductive pattern and the eddy currents produce a secondary magnetic field in the vicinity of the conductive pattern, strength variations of the secondary magnetic field being indicative of line resistance of said conductive pattern and being dominant over any other local magnetic field variations;

magnetic recording means disposed in close proximity to said conductive pattern for capturing an image of said secondary magnetic field; and visualizing means for examining said stored magnetization pattern, wherein said visualizing means comprises a magnetic powder.

4. The apparatus of claim 1, wherein said applying means comprises means for applying a time varying magnetic field.

5. The apparatus of claim 1, wherein said applying means comprises means for applying said rapidly varying magnetic field in a plane of said magnetic recording medium.

6. The apparatus of claim 1, wherein said applying means comprises means for applying said rapidly varying magnetic field perpendicular to said magnetic recording medium.

7. An apparatus for providing a fine line resistance image of a conductive pattern comprising:

means for applying a rapidly varying magnetic field to said conductive pattern such that eddy currents are induced in said conductive pattern and the eddy currents produce a secondary magnetic field in the vicinity of the conductive pattern, strength variations of the secondary magnetic field being indicative of line resistance of said conductive pattern and being dominant over any other local magnetic field variations; and magnetic recording means disposed in close proximity to said conductive pattern for capturing an image of said secondary magnetic field, wherein said magnetic recording means comprises magnetic recording tape.

8. The apparatus of claim 1, wherein said applying means comprises:

a predetermined amount of low conductivity magnetic material having a slot;

a coil passing through said slot; and means for applying a current to said coil.

9. The apparatus of claim 1, wherein said applying means comprises:

a post of low conductivity magnetic material;

a predetermined number of turns of coil wound around said post; and a low conductive return path coupled to said coil.

10. The apparatus of claim 9, wherein said coil comprises a predefined number of turns of wire.

11. The apparatus of claim 1, wherein said applying means applies said rapidly varying magnetic field to a first region of said conductive pattern to be imaged and wherein said apparatus further comprises means for moving said applied magnetic field in order to apply said rapidly varying magnetic field to a second region of said conductive pattern.

12. A method for providing a fine line resistance image of a conductive pattern, said method comprising the steps of:

applying a rapidly varying magnetic field to said conductive pattern such that eddy currents are induced in said conductive pattern and the eddy currents produce a secondary magnetic field in the vicinity of the conductive pattern, strength variations of said secondary magnetic field being indicative of line resistance of said conductive pattern and dominant over any other local magnetic field variations; and directly capturing an image of said secondary magnetic field on a magnetic recording medium.

13. The method of claim 12, wherein said applying step comprises the step of applying a time varying magnetic field.

14. The method of claim 12, wherein said rapidly varying magnetic field is applied perpendicular to said magnetic recording medium.

15. The method of claim 12, wherein said rapidly varying magnetic field is applied in a plane of said magnetic recording medium.

16. The method of claim 12, further comprising the step of placing said magnetic recording medium in close proximity to said conductive pattern.

17. The method of claim 12, further comprising the step of visualizing said captured image.

18. A method for providing a fine line resistance image of a conductive pattern, said method comprising the steps of:

applying a rapidly varying magnetic field to said conductive pattern such that eddy currents are induced in said conductive pattern and the eddy currents produce a secondary magnetic field in the vicinity of the conductive pattern, strength variations of said secondary magnetic field being indicative of line resistance of said conductive pattern and dominant over any other local magnetic field variations;

capturing an image of said secondary magnetic field on a magnetic recording medium; and visualizing said captured image, wherein said visualizing step comprises the step of applying a magnetic powder to said recording medium.

19. A method for providing a fine line resistance image of a conductive pattern, said method comprising the steps of:

applying a rapidly varying magnetic field to said conductive pattern such that eddy currents are induced in said conductive pattern and the eddy currents produce a secondary magnetic field in the vicinity of the conductive pattern, strength variations of said secondary magnetic field being indicative of line resistance of said conductive pattern and dominant over any other local magnetic field variations; and capturing an image of said secondary magnetic field on a magnetic recording medium, wherein said magnetic recording medium comprises magnetic recording tape.

20. The method of claim 12, wherein the rapidly varying magnetic field is applied to a first region of said conductive pattern to be imaged and, wherein said method further comprises the steps of:

moving said applied magnetic field to apply said rapidly varying magnetic field to a second region of said conductive pattern;

applying said rapidly varying magnetic field to said second region of said conductive pattern such that another secondary magnetic field having strength variations indicative of line resistance is produced by eddy currents in said second region of said conductive pattern; and storing an image of said another secondary magnetic field on a magnetic recording medium.

21. The method of claim 20, wherein said second region partially overlaps said first region.

\* \* \* \* \*